United States Patent [19]

Stults et al.

[11] Patent Number: 4,990,670
[45] Date of Patent: Feb. 5, 1991

[54] METHOD OF MAKING 1,1'-OXYBIS (3-NITRO-5-TRIFLUOROMETHYL)-BENZENE

[75] Inventors: Jeffrey S. Stults; Henry C. Lin, both of Grand Island, N.Y.

[73] Assignee: Occidental Chemical Corporation, Niagara Falls, N.Y.

[21] Appl. No.: 394,986

[22] Filed: Aug. 17, 1989

[51] Int. Cl.$^5$ ............... C07C 43/00; C07C 209/00
[52] U.S. Cl. ................... 564/417; 564/418; 568/585
[58] Field of Search ............... 564/417, 418; 568/585

[56] References Cited

U.S. PATENT DOCUMENTS

| | | | |
|---|---|---|---|
| 3,063,962 | 11/1962 | Cyba | 524/246 |
| 3,140,316 | 7/1964 | Towle | 564/418 |
| 3,290,377 | 12/1966 | Appell | 564/417 |
| 3,322,525 | 5/1967 | Martin et al. | 71/98 |
| 3,420,892 | 1/1969 | Martin et al. | 568/585 |
| 3,634,519 | 1/1972 | Bentz et al. | 568/585 |
| 4,179,461 | 12/1979 | Marhold et al. | 558/420 |
| 4,484,008 | 11/1984 | Cook, Jr. et al. | 568/639 |

FOREIGN PATENT DOCUMENTS 55-024125  2/1980  Japan ..................... 568/585

OTHER PUBLICATIONS

March, Jerry, *Advanced Organic Chemistry*, New York: McGraw-Hill Book Company, 1977, p. 462.

Primary Examiner—Glennon H. Hollrah
Assistant Examiner—Scott C. Rand
Attorney, Agent, or Firm—James F. Tao; Richard D. Fuerle

[57] ABSTRACT

Disclosed is a method of making 1,1'-oxybis (3-nitro-5-trifluoromethyl)-benzene by heating a nitro benzofluoride compound having the formula

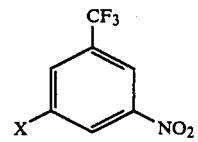

where "X" is selected from the group consisting of $NO_2$, Cl, and F, with an alkali metal fluoride selected from the group consisting of potassium fluoride, cesium fluoride, and mixtures thereof, in an organic solvent in the presence of water. The corresponding diamine, 5,5'-oxybis (3-trifluoromethyl)-benzamine, can be prepared by reducing the benzene compound.

15 Claims, No Drawings

METHOD OF MAKING 1,1'-OXYBIS (3-NITRO-5-TRIFLUOROMETHYL)-BENZENE

BACKGROUND OF INVENTION

The invention relates to a method of making 1,1'-oxybis (3-nitro-5-trifluoromethyl)-benzene by heating 3,5-dinitro-benzotrifluoride. Also disclosed is the reduction of 1,1'-oxybis (3-nitro-5-trifluoromethyl)-benzene to 5,5'-oxybis (3-trifluoromethyl) benzamine.

In patent application Ser. No. 394,990, filed of even date by J. Stults and H. C. Lin, titled "Novel Bis-M Benzotrifluoride Compounds," herein incorporated by reference, there is described the novel compound 1,1'-oxybis (3-nitro-5-trifluoromethyl)-benzene (OBB), and the novel compound 5,5'-oxybis (3-trifluoromethyl)-benzamine, which is made by reducing OBB. The benzamine compound is useful in making polyimides, polyamides, polyamide-imides, and polyurethanes. Polyimides made using the benzamine compound have excellent electronic properties, particularly a high solubility in organic solvents and a low dielectric constant, which make them very useful in the electronics industries. In addition, they also have the properties that polyimides are noted for—outstanding mechanical strength and excellent thermal and oxidative stability.

SUMMARY OF INVENTION

We have discovered that 1,1'-oxybis (3-nitro-5-trifluoromethyl)-benzene

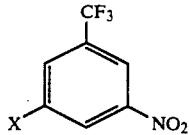

can be made by heating 3,5-dinitrobenzotrifluoride with an alkali metal fluoride in an organic solvent in the presence of water.

That this reaction occurs is quite surprising because the activating groups, the two nitro groups and the single trifluoromethyl group on the 3,5-dinitrobenzotrifluoride, are not in the correct ring position for producing that product. That is, both nitro groups and trifluoromethyl groups are known to activate the ortho and para positions on the benzene ring, and, because they are meta in this compound, one would expect a poor reaction to occur even under harsh conditions. Actually, the reaction is a very good reaction and occurs under mild conditions (temperatures of less than 150° C.)

DESCRIPTION OF INVENTION

The starting material for the process of this invention is a known and commercially available nitro benzotrifluoride compound having the formula:

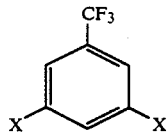

where each "X" is independently selected from $NO_2$, Cl, F, and mixtures thereof. In the preferred starting material "X" is $NO_2$, i.e., the compound is 3,5-dinitrobenzotrifluoride, because that compound is more readily available and $NO_2$ is a better leaving group.

In the preparation of 1,1'-oxybis(3-nitro-5-trifluoromethyl) benzene, according to this invention, the nitrobenzotrifluoride compound is heated in the presence of water with an alkali metal fluoride which can be potassium fluoride, cesium fluoride, or a mixture thereof; potassium fluoride is preferred as it is less expensive. Any organic solvent that will dissolve the starting material can be used, preferably at about 10 to about 50% solids. Examples of suitable solvents include dimethyl formamide, dimethyl acetamide, N-methyl pyrrolidinone, sulfolane, methyl sulfone, dimethyl sulfoxide, and methyl sulfoxide. Amide solvents are preferred, and dimethyl formamide in particular is preferred, as it is inexpensive and is easy to purify and remove. At least ½ equivalent of water, based on the amount of the OBB, should be used. The reaction mixture is heated to a temperature of about 140° to about 210° C. and the reaction can be followed on a gas chromatograph to determine when it is complete. Depending on the temperature, the reaction takes about 1 to about 24 hours. The product can be isolated by distilling off the solvent, extracting the product from water, and crystallizing. A yield greater than 50% can be expected.

The corresponding benzamine compound, 5,5'-oxybis (3-trifluoromethyl)-benzamine, can be prepared by reducing the two nitro groups on OBB to amine groups. The reduction reaction is a relatively simple reaction which can be performed in the presence of a reducing agent, such as a mixture of about 10 to about 50% by weight $Fe^{+3}$ and about 1 to about 20% by weight HCl. Other useful reducing agents include palladium, ammonium sulfide, hydrazine, etc.

The benzamine compound is useful in making polyimides, polyamide-imides, and polyamides. The polyimides can be prepared by well-known reactions of diamines with dianhydrides or tetracarboxylic acids, substituting the benzamine of this invention for a diamine that would otherwise be used. Further information on those reactions can be found in the hereinabove referenced co-pending application Ser. No. 394,990.

The following examples further illustrate this invention.

EXAMPLE 1

To a 500 ml round bottom flask was charged 3,5-dinitrobenzotrifluoride (25.1 g.), potassium fluoride (21.2 g.), water (2.4 ml.), and dimethylformamide (DMF, 125 ml.). The reaction was heated to 160° C. for 24 hours. The reaction mixture was diluted with water (400 ml.) and extracted with ether (3 times with 150 ml.). The ether was dried with magnesium sulfate and cooled to 5° C. The solid was collected and hexane added to the filtrate until the filtrate was cloudy. The filtrate was cooled to 5° C. and the resulting solid collected to give a total of 11.3 g (53.8% yield) of the desired 1,1'-oxybis(3-nitro-5-trifluoromethyl)benzene.

EXAMPLE 2

The following experiment was conducted to determine if the other leaving groups could be used in place of nitro for the preparation of 1,1'-oxybis(3-nitro-5-trifluoromethyl)benzene. To a solution of 3-fluoro-5-nitrobenzotrifluoride, isolated by distillation from the mother liquor of Example 1, in DMF (5 ml.) was added potassium fluoride (0.7 g.). The suspension was heated to 150° C. and 2 drops of water were added. The reaction progress was monitored by gas chromatography (GC). After 7 hours, GC analysis indicated that a 0.17:1 mixture of 1,1′-oxybis(3-nitro-5-trifluoromethyl)benzene to the starting fluoride had been obtained. This ratio increased to 2.1:1 after heating for 17.5 hours.

We claim:

1.

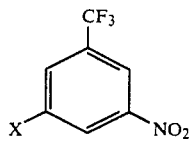

where "X" is selected from the group consisting of $NO_2$, Cl, and F, with an alkali metal fluoride selected from the group consisting of potassium fluoride, cesium fluoride, and mixtures thereof, in an organic solvent in the presence of water.

2. A method according to claim 1 wherein "X" is $NO_2$.

3. A method according to claim 1 wherein said alkali metal fluoride is potassium fluoride.

4. A method according to claim 1 wherein said nitro benzotrifluoride is heated at a temperature of about 140° to about 210° C.

5. A method according to claim 1 wherein said organic solvent is an amide.

6. A method according to claim 5 wherein said organic solvent is dimethyl formamide.

7. A method according to claim 1 including the additional last step of distilling off said organic solvent and crystallizing said 1,1′-oxybis (3-nitro-5-trifluoromethyl)-benzene.

8. A method of making 1,1′-oxybis (3-nitro-5-trifluoromethyl)-benzene comprising heating 3,5-dinitrobenzotrifluoride to a temperature of about 140° to about 210° C. with potassium fluoride in an amide solvent in the presence of at least ½ equivalent of water, based on the amount of said 1,1′-oxybis (3-nitro-5-trifluoromethyl)-benzene.

9. A method of making 5,5′-oxybis(3-trifluoromethyl)-benzamine comprising (1) heating a nitro-benzotrifluoride compound having the formula

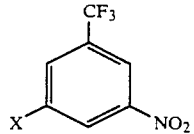

where "X" is selected from the group consisting of $NO_2$, Cl, and F, with an alkali metal fluoride selected from the group consisting of potassium fluoride, cesium fluoride, and mixtures thereof, in an organic solvent in the presence of water; and (2) reducing said 1,1′-oxybis(3-trifluoromethyl-benzene to 5,5′-oxybis(3-trifluoromethyl)-benzamine.

10. A method according to claim 9 wherein "X" is $NO_2$.

11. A method according to claim 9 wherein said reduction is performed by heating in the presence of about 10 to about 50% by weight $Fe^{+3}$ and about 1 to about 20% by weight HCl.

12. A method according to claim 1 wherein "X" is Cl.
13. A method according to claim 1 wherein "X" is F.
14. A method according to claim 9 wherein "X" is Cl.
15. A method according to claim 9 wherein "X" is F.

* * * * *

UNITED STATES PATENT AND TRADEMARK OFFICE
CERTIFICATE OF CORRECTION

PATENT NO. : 4,990,670

DATED : February 5, 1991

INVENTOR(S) : Jeffrey S. Stults; Henry C. Lin

It is certified that error appears in the above-identified patent and that said Letters Patent is hereby corrected as shown below:

Column 1, line 35, delete the formula and substitute---

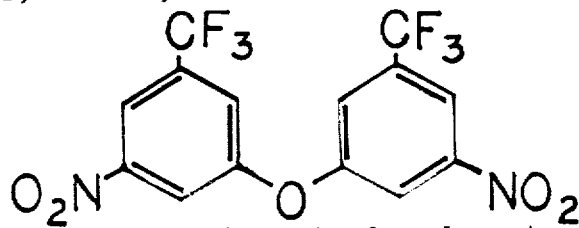

Column 1, line 62, delete the formula and substitute---

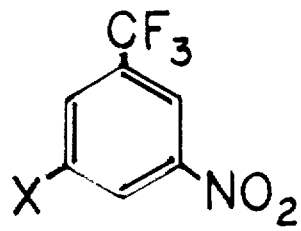

Column 1, lines 66 to 67, delete "each "X" is independently selected from $NO_2$, Cl, F, and mixtures thereof" and substitute ---"X" is $NO_2$, Cl, or F.---

UNITED STATES PATENT AND TRADEMARK OFFICE
CERTIFICATE OF CORRECTION

PATENT NO. : 4,990,670

DATED : February 5, 1991

INVENTOR(S) : Jeffrey S. Stults: Henry C. Lin

It is certified that error appears in the above-identified patent and that said Letters Patent is hereby corrected as shown below:

Column 3, line 10, Claim 1, prior to the formula, insert --A method of making 1,1'-oxybis (3-nitro-5-trifluoromethyl)-benzen comprising heating a nitro-benzo-trifluoride compound having the formula--.

Signed and Sealed this

Fourteenth Day of July, 1992

Attest:

DOUGLAS B. COMER

Attesting Officer

Acting Commissioner of Patents and Trademarks